United States Patent
Heyman et al.

(10) Patent No.: US 7,017,422 B2
(45) Date of Patent: Mar. 28, 2006

(54) BOND TESTING SYSTEM, METHOD, AND APPARATUS

(75) Inventors: Joseph S. Heyman, Williamsburg, VA (US); John E. Lynch, Williamsburg, VA (US)

(73) Assignee: Luna Innovations Incorporated, Blacksburg, VA (US)

( * ) Notice: Subject to any disclaimer, the term of this patent is extended or adjusted under 35 U.S.C. 154(b) by 0 days.

(21) Appl. No.: 10/816,667

(22) Filed: Apr. 2, 2004

(65) Prior Publication Data

US 2005/0217388 A1 Oct. 6, 2005

(51) Int. Cl.
*G01N 3/08* (2006.01)

(52) U.S. Cl. .......................................... 73/827
(58) Field of Classification Search .................. 73/827, 73/834, 837, 761
See application file for complete search history.

(56) References Cited

U.S. PATENT DOCUMENTS

| | | | |
|---|---|---|---|
| 3,003,351 A | 10/1961 | Ziegler et al. | |
| 4,015,464 A | 4/1977 | Miller et al. | |
| 4,062,227 A | 12/1977 | Heyman | |
| 4,117,731 A | 10/1978 | Heyman | |
| 4,213,183 A | 7/1980 | Barron et al. | |
| 4,363,242 A | 12/1982 | Heyman | |
| 4,372,163 A * | 2/1983 | Tittmann et al. | 73/602 |
| 4,538,462 A | 9/1985 | Hartog et al. | |
| 4,593,565 A | 6/1986 | Chamuel | |
| 4,624,142 A | 11/1986 | Heyman | |
| 4,750,368 A | 6/1988 | Shearer et al. | |
| 4,817,016 A | 3/1989 | Thompson et al. | |
| 4,843,346 A | 6/1989 | Heyman et al. | |
| 4,856,334 A | 8/1989 | Shearer et al. | |
| 5,237,516 A | 8/1993 | Heyman | |
| 5,357,423 A * | 10/1994 | Weaver et al. | 700/28 |
| 5,396,799 A | 3/1995 | Ross et al. | |
| 5,431,324 A * | 7/1995 | Kajiwara et al. | 228/102 |
| 5,847,284 A * | 12/1998 | Theller | 73/827 |
| 6,490,047 B1 * | 12/2002 | Siu | 356/502 |
| 6,543,668 B1 * | 4/2003 | Fujii et al. | 228/103 |

OTHER PUBLICATIONS

Provisional Patent Application of Heyman et al.; "A Differential Guided Wave Nonlinear Spectroscopy System;" Ser. No. 60/476,218; filed Jun. 6, 2003.

Patent Application of Heyman et al.; "Method and Apparatus for Determining and Assessing a Characteristic of a Material;" Ser. No. 10/860,636; filed Jun. 4, 2004.

Joseph S. Heyman; "Residual Stress Characterization with a Magnetic/Ultrasonic Technique;" proceedings of IEEE, 1984 Ultrasonics Symposium, Dallas, TX; Nov. 14-16, 1984; pp. 950-954.

(Continued)

*Primary Examiner*—Max Noori
(74) *Attorney, Agent, or Firm*—Nixon & Vanderhye P.C.

(57) ABSTRACT

A bond strength tester and method for determining certain bond strength parameters of a bonded component, including a phaselocker, a transducer, a loading device that is capable of applying stress-loads to the bond, a controller for controlling the loading device, a data recording device to acquire data, and a computer device to analyze data calculating certain bond strength parameters.

32 Claims, 6 Drawing Sheets

OTHER PUBLICATIONS

Sidney G. Allison, Joseph S. Heyman, and K. Salama; "Ultrasonic Measurement of Residual Deformation Stress in Thin Metal Plates Using Surface Acoustic Waves;" proceedings of IEEE 1983 Symposium, Atlanta, GA; Oct. 31-Nov. 2, 1983; pp. 995-999.

Joseph S. Heyman and Larry L. Yoder; "An Interferometric Measurement of the Acoustoelastic Constant of Rock Core Samples;" proceedings of IEEE, 1983 Symposium, Atlanta, GA; Oct. 31-Nov. 2, 1983; pp. 980-983.

Joseph S. Heyman and Wolfgang Issler; "Ultrasonic Mapping of Internal Stresses;" proceedings of IEEE 1982 Ultrasonic Symposium, San Diego, CA; Oct. 27-29, 1982; pp. 893-897.

Joseph S. Heyman; "A CW Ultrasonic Bolt-Strain Monitor," SESA Experimental Mechanics, 17; 1977; p. 183.

J.E. Lynch, J.S. Heyman, and A.R. Hargens; "Ultrasonic Device for the Noninvasive Diagnosis of Compartment Syndrome;" Physiological Measurement, vol. 25, Issue 1, 2004; pp. N1-N9.

Robert S. Rogowski, Milford S. Holben, Patrick Sullivan, and Joseph S. Heyman; "A Method for Monitoring Strain in Large Structures: Optical and Radio Frequency Devices;" presented at the Review of Progress in Quantitative Nondestructive Evaluation, Williamsburg, VA; Jun. 21-26, 1987; pp. 559-563.

Sidney G. Allison, Joseph S. Heyman, Min Namkung, and K. Salama; "Ultrasonic Characterization of Plastic Deformation in Metals;" Review of Progress in Quantitative NDE; Plenum Press, New York (1986); pp. 1565-1573.

"Pulsed Phase-Locked-Loop Strain Monitor" A high-resolution, fully-automated strain monitor; NASA Tech Brief; Langley Research Center, Hampton, VA; Spring 1981, B-81-10068, LAR-12772.

S.G. Allison, J. S. Heyman, K. Smith, and K. Salama; "Effect of Prestrain Upon Acoustoelasetic Properties of Carbon Steel;" 1984 Ultrasonics Symposium; NASA Langley Research Center, Hampton, VA; pp. 997-1002.

J. Frankel and W. Scholz; "Ultrasonic Studies of Stresses and Plastic Deformation in Steel During Tension and Compression;" US Army Armament Research, Development, & Engineering Ctr., Watervliet, NY; pp. 1577-1584.

J. S. Heyman, S. G. Allison, and K. Salama: "Influence of Carbon Content on Higher-Order Ultrasonic Properties in Steels;" 1983 Ultrasonics Symposium; NASA-Langley Research Center, Hampton, VA; University of Houston, TX; pp. 991-994.

M. Namkung, R. DeNale, and D. Utrata; "Uniaxial Stress and Wave Mode Dependence of Magnetoacoustic Responses in Iron-Base Alloys;" NASA Langley Research Center, Hampton, VA.

International Search Report and Written Opinion mailed Oct. 13, 2005 in corresponding PCT Application PCT/US05/10445.

* cited by examiner

BOND TESTING SYSTEM, METHOD, AND APPARATUS

BACKGROUND OF THE INVENTION

1. Field of the Invention

This invention relates generally to nondestructive testing and assessment. In particular, the present invention relates to nondestructive testing and assessment of bonds and bond strength.

2. Description of Related Art

Accurate and effective nondestructive bond strength evaluation has been one of the more challenging and elusive nondestructive goals for decades. In certain aerospace sectors, bond testing has been done using an approach that determines the percent area covered by the bond. An assumption made by the percent area approach is that any area that is not covered by a bond has no strength and any area that is covered by a bond has full bond strength. Unfortunately, some "bonds" exist that are in physical contact, but have no strength. These are often referred to as "kissing bonds" and offer no strength but are measured by the percent area approach as fully strong.

The need for a technique to assess bond strength is significant. Bonds are an important structural element in many designs. A fully bonded structure is less costly to build, is lower in weight and offers improved fatigue properties over a similar structure with fasteners.

Aircraft structures are a good example of a critical geometry that benefits from full bonding. Since bonds are not sufficiently reliable, an aircraft structure uses both bonds and rivets to complete the structural assembly. For example, Lockheed Martin's KC-130 aircraft uses 500,000 rivets. A fully bonded structure without redundant rivets would have a significant cost and weight savings in addition to enhanced safety.

There are other geometries that cannot use redundant fastening. For example, solid-rocket motors use a bonded insulation to separate the burning fuel from the outer casing. Currently, there are no quantitative measurement systems to directly assess the bond quality of flight worthy components and quality assurance for such systems depends solely on process control.

Bonding is also an important part of commercial fabrication. Automotive systems use significant bonding during assembly. Furniture, sports equipment, and boating equipment all benefit from bonded assemblies. Bonding is a significant medical technique for some procedures. Yet, the technology for bond assessment is unable to verify strength in a given part.

Ultrasonics is one of the primary nondestructive approaches to assessing bond quality. Both pulse-echo as well as continuous wave resonance ultrasonic tests have been used to assess bond strength to varying degrees of success. Ultrasonic tests measure the reflected and/or transmitted wave energy that interacts with the bond. Typically, such tests determine geometric properties, such as voids. However, such tests cannot verify bond strength.

Thermography is another testing method that has had limited success. Similar to scanning ultrasonics, thermography cannot distinguish a kissing bond from a good bond.

An engineering approach to bond testing is spot sampling. Using this method, a component, or witness sample, is selected from a production line and tested to failure. The failure loads experienced by the witness sample are assumed to represent the failure load for all of the components that has been produced since the testing of the last witness sample.

Witness sampling has two major failings. First, all components since the last witness sample test are suspect and should be identified as such. That requires witness sample inventory and idle parts. Second, a specific witness sample might not accurately represent all of the output components.

A weak bond may be in use where a failure may be catastrophic. Therefore, witness sample techniques drive process costs to maintain very tight constraints on quality, a desired outcome, but at a cost that may exceed the return on investment when compared to the systems, methods, and apparatuses of this invention.

SUMMARY OF THE INVENTION

High quality is a goal that might be reached at lower costs if the process variables that are measured directly link to the desired outcomes, namely strength. Today, one sees other variables linked to the bonding process control feedback such as temperature, time, pressure, vacuum and others. All are important, but not directly linked to strength.

Thus, the present invention relates generally to the nondestructive assessment of bond strength between two members. The invention is a measurement system comprised of an ultrasonic system (including a phaselocker), a stressing system, and a controlling/data processing system. The systems, methods, and apparatuses of this invention measure changes in the nonlinear anelastic material properties of the bond material using ultra-sensitive acoustic phase-locking propagation coupled to a controlled state-change, such as stress. Bond strength is determined from statistical comparisons with similar geometry sample tests characterized with this technique and subsequently loaded to failure.

During operation of the systems, methods, and apparatuses of this invention, the phaselocker is coupled, via a transducer, to a bonded system. Then, the transducer and phaselocker frequency lock to the ultrasonic phase condition of the bonded system.

A data monitoring and acquisition circuit acquires and averages ultrasonic frequency data. Then, the bond strength tester applies stress to the bonded system, holds that stress for a period of time, and then relaxes the stress back to the initial condition. Before, during, and after the stress is applied to the bond, the data monitoring and acquisition circuit acquires the corresponding ultrasonic frequency of the locked phaselocker.

The applied stress alters the phase-locking frequency and at least three measured changes occur in the bonded system. First, the bond is stretched producing a longer acoustic propagation path. Second, the stress field alters the acoustic velocity of sound. Third, there are time dependent relaxation effects caused by the change in the stress field. Some of these effects are reversible while others are indicative of permanent changes.

The bond strength tester determines the time dependant changes in the bonded system phase state. Bonds of high strength behave in a fashion that is predicable and repeatable. Questionable bonds exhibit properties clearly different from high strength bonds and may be identified without taking the bond to loads that would damage a good bond.

Accordingly, this invention provides a bond strength tester, which generates a nondestructive measurement parameter that is linked to bond strength for process control.

This invention separately provides a bond strength tester, which obtains measurements without damaging a fabricated part, such that witness samples may no longer be required.

This invention separately provides a bond strength tester, which provides quantitative information about the bond physics.

This invention separately provides a bond strength tester, which, when combined with witness tests data from given materials and geometries, provides bond strength parameters that are a predictor of bond strength.

This invention separately provides a bond strength tester, which allows each production component to be tested rather than relying on a statistical projection of component performance.

This invention separately provides a bond strength tester, wherein the bond strength of a bonded system or component may be assessed after the component has been in use. The re-certification of a component enables life assessment and perhaps life extension based on a review of the condition of all components in the structural assembly and their interactions. Using the systems, methods, and apparatuses of this invention, re-certification of a component may be achieved through analyzing and determining the link between the nonlinear ultrasonic parameter and bond strength itself.

This invention separately provides a bond strength tester, wherein measurements may be provided that may be used to determine the remaining life of a given bond assembly through periodic characterization of the bond over time. In this manner, degradation in strength over the life of a component may be monitored and used to schedule maintenance and/or retirement of the component instead of maintenance and/or retirement based on a linear time base or cycles of use.

These and other features and advantages of this invention are described in or are apparent from the following detailed description of the exemplary embodiments.

BRIEF DESCRIPTION OF THE DRAWINGS

The exemplary embodiments of this invention will be described in detail, with reference to the following figures, wherein like reference numerals refer to like parts throughout the several views, and wherein.

DETAILED DESCRIPTION OF THE PREFERRED EMBODIMENT

For simplicity and clarification, the operating principles, design factors, and layout of the bond strength testing systems, methods, and apparatuses according to this invention are explained with reference to various exemplary embodiments of bond strength testing systems, methods, and apparatuses according to this invention. The basic explanation of the operation of the bond strength testing systems, methods, and apparatuses is applicable for the understanding and design of the constituent components employed in the bond strength testing systems, methods, and apparatuses of this invention.

Figure 1:
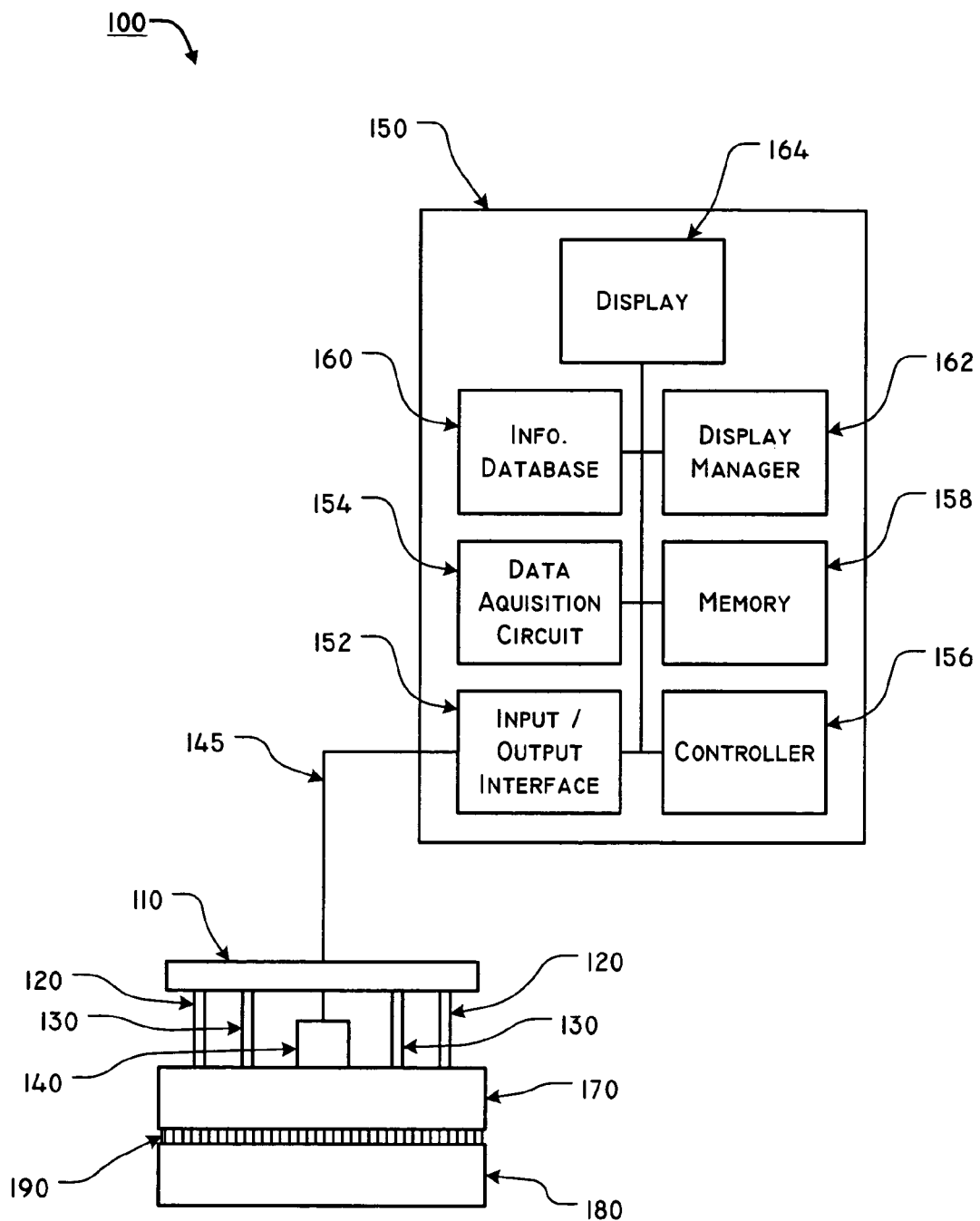
FIG. 1 shows a first exemplary embodiment of a bond strength tester according to this invention.

FIG. 1 shows a first exemplary embodiment of a bond strength tester 100 according to this invention. As shown in FIG. 1, the bond strength tester 100 includes at least some of a coupler 110, a force reactor 120, a stressor 130, a transducer 140, and a phaselocker 150.

The coupler 110 integrates the force reactor 120 and the stressor 130, such that each of the force reactor 120 and the stressor 130 are capable of being actuated and/or manipulated by the controller 156.

The force reactor 120 is capable of being attached to a bonded component. The force reactor 120 provides the reaction force to the stressor 130 for the exemplary embodiments including both the force reactor 120 and the stressor 130 on the tested bond structure. The force reactor 120 can be, for example, a plastic rod that will undergo compression in response to the tension of the stressor 130.

The stressor 130 is able to apply a load or force to the bonded component following a prescribed loading sequence. The stressor 130 can have a vacuum, a bond joint, a magnetic chuck, or other attachment depending on the first bondplate 170 material. The stressor 130 may include a screw device that shortens in length providing a pull-force on the first bondplate 170 material through the chuck reacting through the force reactor 120. Similarly, the force reactor 120 may be an electromotive device that pulls on the chuck.

The transducer 140 is capable of converting, for example, electrical radio frequency signals to ultrasonic, acoustic waves. In various exemplary embodiments, the transducer may be capable of generating and transmitting a compressional or shear wave as a pulse, a tone burst, a continuous wave, or a guided wave. Additionally, in various exemplary embodiments, the transducer 140 may include multiple units. It should be appreciated that the transducer 140 may be any known or later developed device capable of converting electrical signals to acoustic waves.

As shown in FIG. 1, the phaselocker 150 may include at least some of an input/output interface 152, a data monitoring and acquisition circuit 154, a controller 156, a memory 158, an information database 160, a display manager 162, and a display 164. The phaselocker 150 interfaces with the transducer 140, via a linked connection 145, through the input/output interface 152.

In various exemplary embodiments, the phaselocker 150 is a high-resolution ultrasonic interferometer system, a transmission/reflection oscillator ultrasonic spectrometer, or a pulsed-phase-locked-loop ultrasonic spectrometer, such as, for example, the pulsed-phase-locked-loop monitor disclosed in U.S. Pat. No. 4,117,731 to Heyman or U.S. Pat. No. 4,363,242 to Heyman. In these various exemplary embodiments, any elements described as being optionally included in the various exemplary embodiments of the phaselocker 150 (i.e., the input/output interface 152, the data monitoring and acquisition circuit 154, the controller 156, the memory 158, the information database 160, the display manager 162, and the display 164), may optionally be operatively coupled to the phaselocker 150 as, for example a computer device.

In various exemplary embodiments, the memory 158 may be implemented using any appropriate combination of alterable, volatile or non-volatile memory or non-alterable, or fixed, memory. The alterable memory, whether volatile or non-volatile, may be implemented using any one or more of non-selectable or dynamic RAM, a floppy disk and disk drive, a writable or re-writable optical disk and disk drive, a hard drive, flash memory or the like. Similarly, the non-alterable or fixed memory may be implemented using any one or more of ROM, PROM, EPROM, EEPROM, an optical ROM disk, such as a CD-ROM or DVD-ROM disk, and disk drive or the like.

In various exemplary embodiments, the memory 158 stores software and data including a software program and specific algorithms used by the bond strength tester 100. For example, the memory 158 may store certain ultrasonic wave propagation and determination software and certain display software. Wave propagation and determination software and display software are familiar to those of ordinary skill in the art.

The data monitoring and acquisition circuit 154 monitors incoming data and/or signal information from the transducer 140 as well as outgoing data and/or signal information to the transducer 140.

The controller 156 manages reading data from and writing data to the memory 158 and drives or manages the transmission of data and/or signal information to and the reception of data and/or signal information from the transducer 140, through the input/output interface 152.

The controller 156 also drives or manages operation of the force reactor 120 and the stressor 130, such that the force reactor 120 and the stressor 130 are capable of being actuated and/or manipulated in concert, by the controller 156, to apply a load or force to a bonded component, following a prescribed loading sequence.

The information database 160 may store at least some data and/or signal information, such as, for example, data and/or signal processing, generation, interpretation, or analysis information. In various exemplary embodiments, the information database 160 may store at least some data and/or information for transfer to the data monitoring and acquisition circuit 154 or that is received from the data monitoring and acquisition circuit 154. The information database 160 may store at least some data and/or signal information obtained from prior tests of particular components for comparison to immediate or future test information of the same or similar components.

In various exemplary embodiments, the display manager 162 drives the display 164. The display 164 may be a cathode ray tube display, a liquid crystal display, a plasma display, a light emitting diode (LED) display, or any other known or later developed system capable of displaying data.

It should be understood that each of the elements of the phaselocker 150, as shown in FIG. 1, may be implemented as portions of a suitably programmed general-purpose computer. Alternatively, each of the elements of the phaselocker 150 shown in FIG. 1 can be implemented as physically distinct hardware circuits within an ASIC, or using a FPGA, a PDL, a PLA or a PAL, or using discrete logic elements or discrete circuit elements. The particular form that each of the elements of the phaselocker 150 will take is a design choice and will be predicable to those skilled in the art.

Moreover, the phaselocker 150 may be implemented as software executing on a programmed general-purpose computer, a special purpose computer, a microprocessor or the like. In this case, the phaselocker 150 may be implemented by physically incorporating it into a software and/or hardware system, such as the hardware or firmware systems of another personal digital assistant, bi-directional pager, analog or digital cellular phone, or the like. The phaselocker 150 may also be implemented as a routine embedded in a network client, as a resource residing on a network server, or the like.

Thus, in summary, the phaselocker 150 may be implemented on a programmed general purpose computer, a special purpose computer, a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA or PAL, or the like. In general, any device, capable of implementing a finite state machine that is in turn capable of implementing the flowchart shown in FIG. 2 may be used to implement the phaselocker 150.

In the various exemplary embodiments described herein, the phaselocker 150 interfaces, for example, with the transducer 140, through the linked connection 145 using the input/output interface 152. Alternatively, the phaselocker 150 may interface with the transducer 140, through a direct wired connection. The linked connection 145 may be any known or later developed device or system for connecting the phaselocker 150 to the transducer 140, including a wireless link, a connection over a LAN, a WAN, or any other distributed network, a connection over the public switched telephone network, a connection over a coaxial cable (i.e., CATV) system, a connection over a cellular telephone network, a very high frequency (VHF) connection, an ultra high frequency (UHF) connection, a radio frequency (RF) connection, a satellite connection, or the like. In general, the linked connection 145 may be any known or later developed connection system or structure usable to connect the phaselocker 150 to the transducer 140, including both wired and wireless connections.

In the various exemplary embodiments described herein, the phaselocker 150 interfaces, for example, with the transducer 140, through a direct Wired connection. Alternatively, the phaselocker 150 may interface with the transducer 140 and/or any other device or database, through a linked connection, as described above, using the input/output interface 152.

It should be appreciated that, in various exemplary embodiments, any of the data monitoring and acquisition circuit 154, the controller 156, the memory 158, the information database 160, the display manager 162, or the display 164 may be located remote from the phaselocker 150 and accessed by the phaselocker 150, via the input/output interface 152.

In various exemplary embodiments, the bond strength tester 100 will be included as part of the software executing on the computer or CPU. It should be appreciated that any other known or later developed system capable of processing and outputting data and/or signal information could be used in place of the computer or CPU. Appropriate software for coordinating with, for example, the display 164 and displaying the graph data and/or signal information is available and understood by those of ordinary skill in the art.

During operation of one exemplary embodiment of the bond strength tester 100, the force reactor 120 is attached to the bonded component. In various exemplary embodiments, the bonded component comprises a first bondplate 170 and a second bondplate 180, which are bonded by a bond material 190.

In the exemplary embodiment shown in FIG. 1, the force reactor 120 is attached to the first bondplate 170. It should be appreciated that the force reactor 120 may be attached to any portion of the bonded component and may be attached by vacuum or any other means or method.

When the force reactor 120 is attached to the bonded component, the force reactor 120 is able to act in correspondence with the stressor 130, such that the stressor 130 is able to apply a load or force to the bonded component, and, more specifically, the bond material 190 following a prescribed loading sequence. Likewise, the stressing force may be applied and measured externally pulling on the coupler 110 through, for example, a force gage that reports to the controller 156.

It should be appreciated that both the force reactor 120 and the stressor 130 are attached to a coupler 110 and are capable of being actuated and/or manipulated by the controller 156.

An ultrasonic transducer 140 is coupled or attached to an appropriate portion of the bonded component and is coupled, via the linked connection 145, to the phaselocker 150.

When the appropriate components are coupled or attached to the bonded component, the bond strength tester 100 is capable of measuring the bond strength of the bond material 190 between the first bondplate 170 and the second bondplate 180.

In various exemplary embodiments of the bond strength tester 100, dual transducers and/or guided-wave transducers may be used for feedback, such that the phaselocker 150 may sample the bond and the bond material 190 in a variety of ways in transmission, reflection, and in resonance. Shear wave transducers and/or compressional wave devices may also be used.

The bond strength tester 100 provides a unique characterization of the bond and the bond material 190 that is based on physical parameters directly linked to strength. The parameters are associated with the polymer chain-links and their stability under stress, their chain straightening caused by strain and chain deformation under load.

In various exemplary embodiments, the bond strength tester 100 is capable of altering the temperature of the bond and/or the bond material 190 in a prescribed fashion while taking temperature data with or without load data and ultrasonic frequency data to determine bond parameters as a function of temperature. In this manner the bond strength tester 100 may determine certain elements of the thermodynamic physics of the bond and the bond material 190 under load and may identify certain bond strength parameters from load, ultrasonic, and thermal data.

When a bond is loaded, it's elastic elongation results in a temperature drop, similar to what occurs when a gas expands. Thermal diffusion brings the bond back to equilibrium with the environment. When the bond is unloaded, the bond will end up at a temperature above its initial condition. The bond will then, again, through diffusion, equilibrate. For plastic deformation, energy is released by the bond generating heat. Thus, plasticity results in the opposite effect caused by thermodynamic stress-induced cooling.

The bond strength tester 100 captures the strain and thermodynamic effects that are occurring in the bond and the bond material 190.

Figure 2:
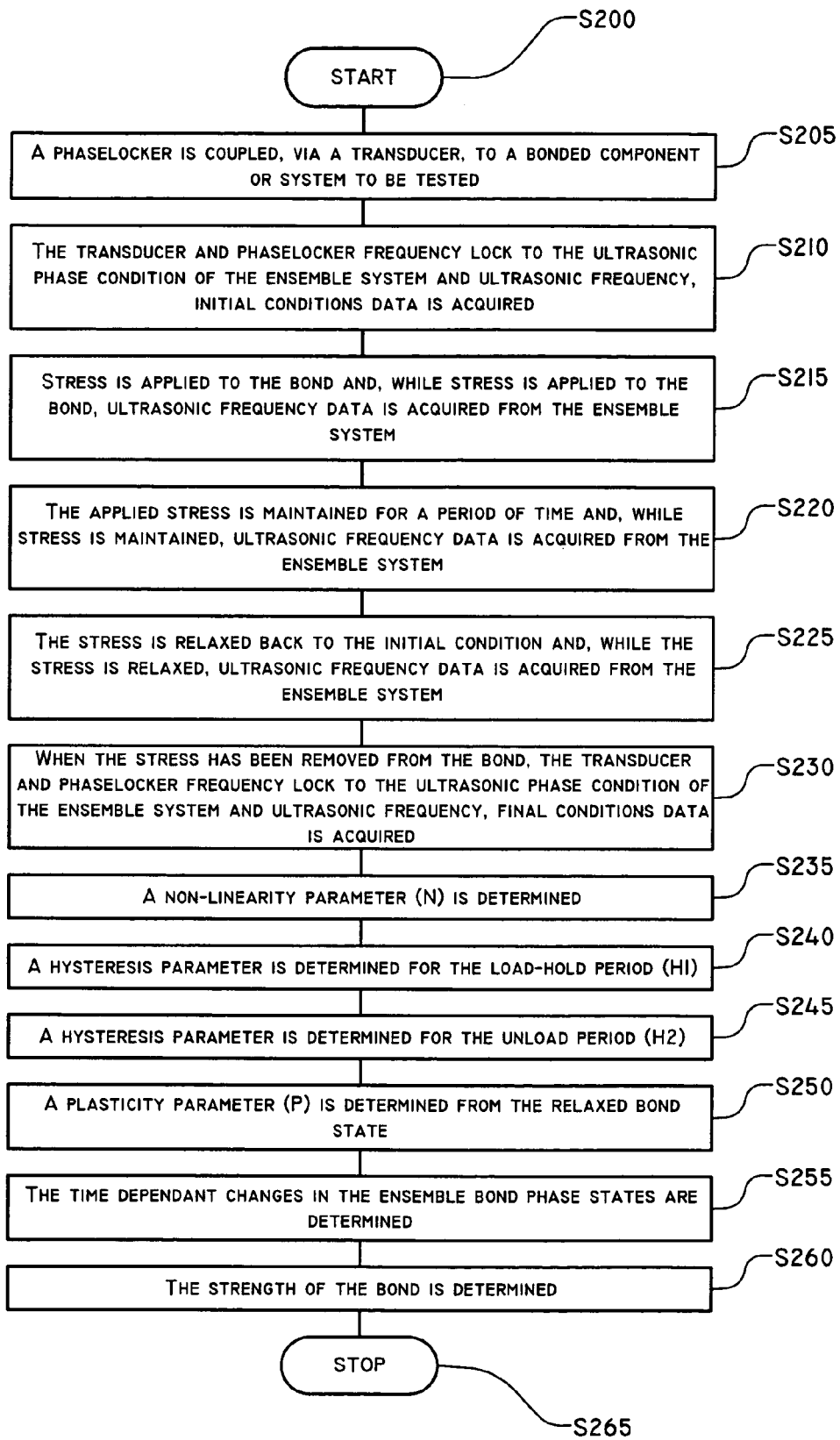
FIG. 2 shows is a flowchart outlining one exemplary embodiment of a method for using the bond strength tester according to this invention.

FIG. 2 is a flowchart outlining one exemplary embodiment of a method for using the bond strength tester according to this invention.

As shown in FIG. 2, beginning in step S200, control continues to step S205, where a phaselocker is coupled, via a transducer, to a bonded component or system to be tested. Next, in step S210, the transducer and phaselocker frequency lock to the ultrasonic phase condition of the ensemble system (including the transducer, the bonded components, the bonds, any connectors, and the phaselocker) and a data monitoring and acquisition circuit acquires at least some load data and ultrasonic frequency, initial conditions data for the ensemble system.

In various exemplary embodiments, the transducer transmits a compressional or shear wave as a pulse, a tone burst, a continuous wave, or a guided wave.

In various exemplary embodiments, a data monitoring and acquisition circuit acquires and averages the initial conditions data with a frequency resolution of parts in ten million Hertz. It should be appreciated that in step S210, the bond strength tester may save, transmit, and/or display at least some information and/or data regarding the acquired initial conditions data for the ensemble system. Control then advances to step S215.

In step S215, the bond strength tester applies an external load to the bonded component by placing the bond under tension or compression, thereby applying stress to the bond (a load period). While stress is being applied to the bond, the data monitoring and acquisition circuit acquires at least some load data and ultrasonic frequency data from the ensemble system. It should be appreciated that in step S215, the bond strength tester may save, transmit, and/or display at least some information and/or data regarding the acquired load data and ultrasonic frequency data for the load period. Control then advances to step S220.

In step S220, the bond strength tester maintains the external load, thereby maintaining the applied stress on the bond for a period of time (a load-hold period). The load-hold period for any particular bond or ensemble system depends on the bond material, but may be on the order of minutes for most materials. While stress is maintained on the bond, the data monitoring and acquisition circuit acquires at least some load data and ultrasonic frequency data from the ensemble system. It should be appreciated that in step S220, the bond strength tester may save, transmit, and/or display at least some information and/or data regarding the acquired load data and ultrasonic frequency data for the load-hold period. Control then advances to step S225.

In step S225, the bond strength tester removes the external load, thereby relaxing the stress on the bond back to the initial condition (an unload period). During the relaxation period, or unload period, while stress is removed from the bond, the data monitoring and acquisition circuit acquires at least some load data and ultrasonic frequency data from the ensemble system. It should be appreciated that in step S225, the bond strength tester may save, transmit, and/or display at least some information and/or data regarding the acquired load data and ultrasonic frequency data for the unload period. Control then advances to step S230.

In step S230, when the stress has been removed from the bond, the transducer and phaselocker frequency data monitoring and acquisition circuit acquires at least some load data and ultrasonic frequency, final conditions data. It should be appreciated that in step S230, the bond strength tester may save, transmit, and/or display at least some information and/or data regarding the acquired ultrasonic frequency, final conditions data.

Figure 3:
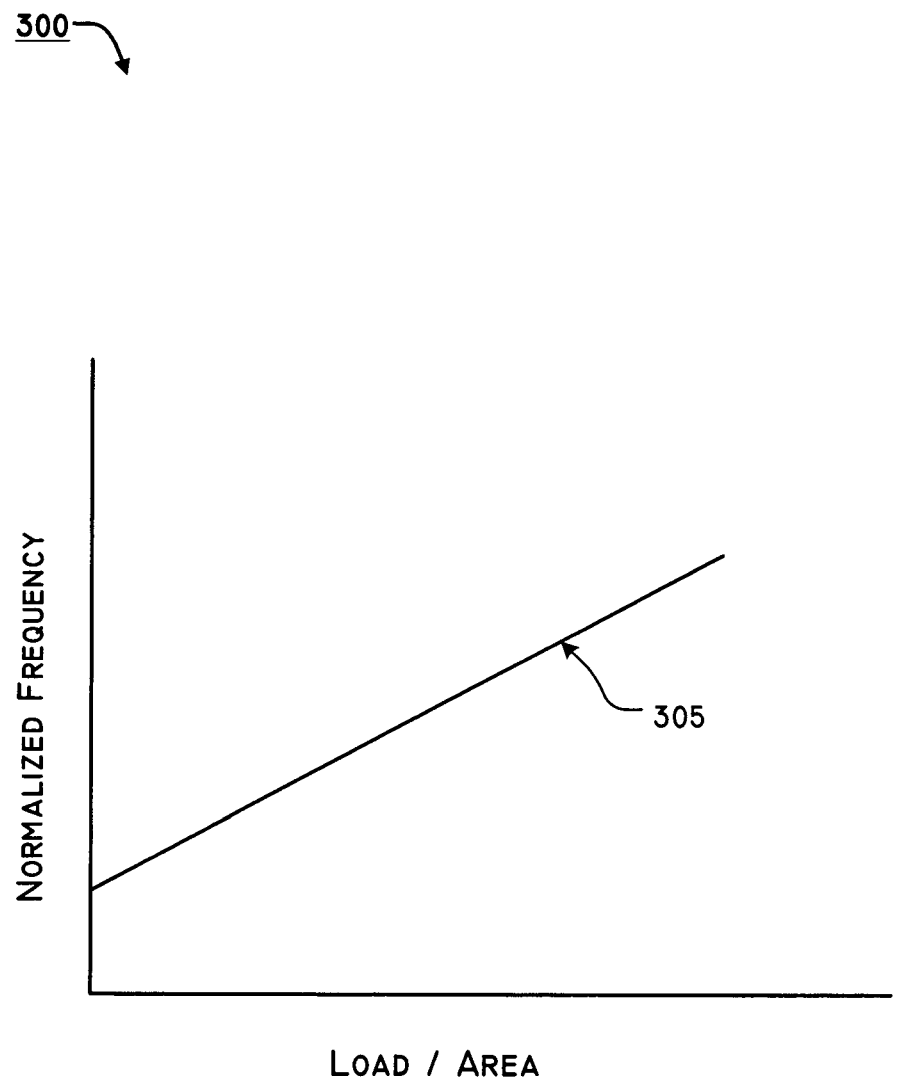
FIG. 3 shows the typical data and/or signal information that is used for determining a value of the non-linearity parameter (N), according to this invention.
Figure 4:
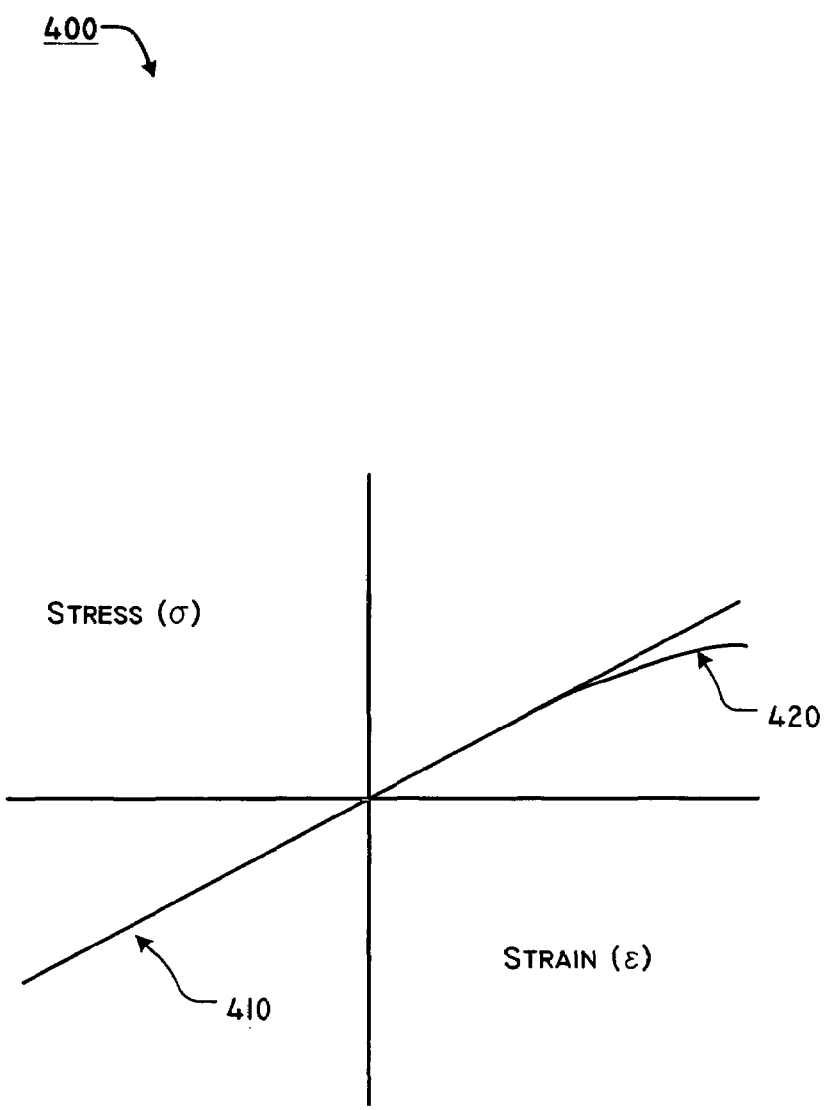
FIG. 4 shows a region of an exemplary stress-strain curve where a bond exhibits nonlinear strain.
Figure 5:
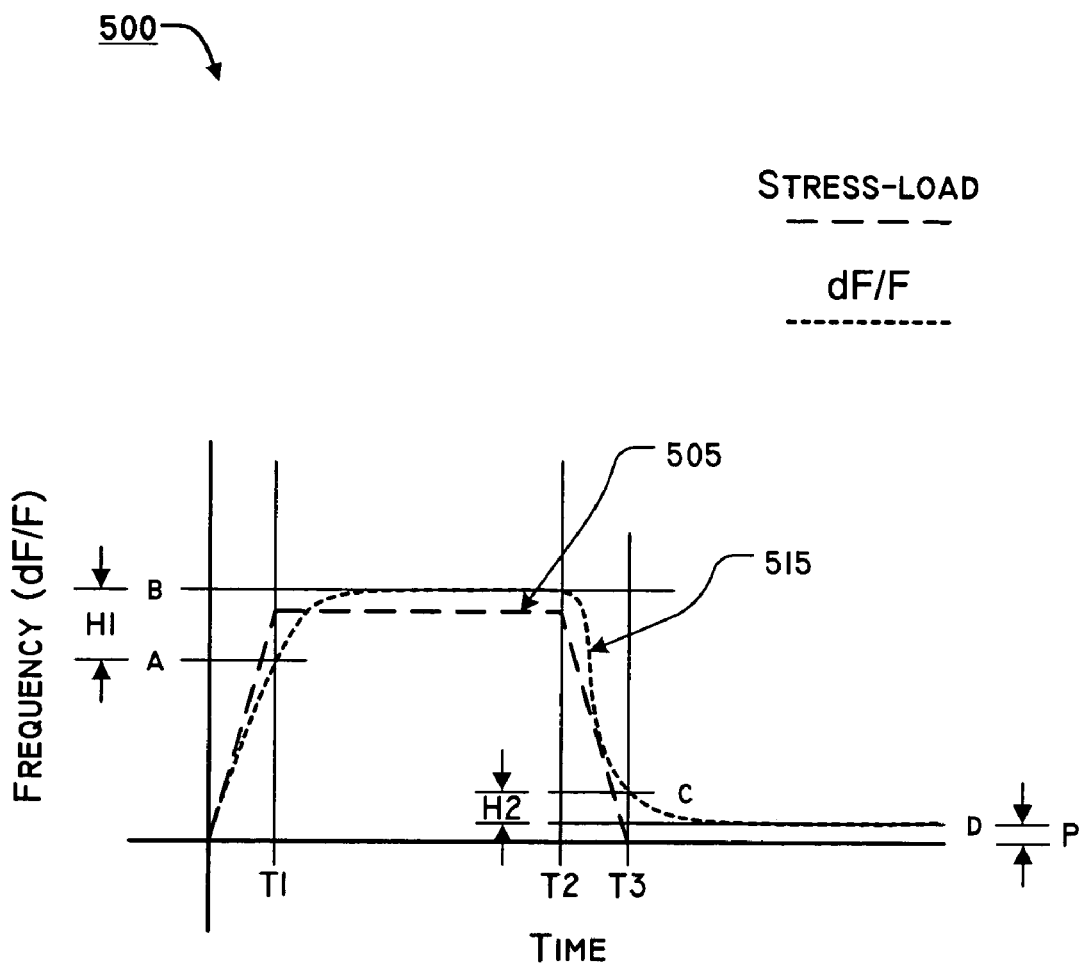
FIG. 5 shows an exemplary data run with hysteresis and plasticity.

Then, in step S235, a non-linearity parameter (N) is determined, as described in greater detail with respect to FIGS. 3–5. N is the normalized frequency shift divided by the load per unit bond area. It should be appreciated that in step S235, the bond strength tester may save, transmit, and/or display at least some information and/or data regarding the determined non-linearity parameter, N. Control then advances to step S240.

In step S240, a hysteresis parameter (H1) is determined for the load-hold period, as described in greater detail with respect to FIG. 5. Then, in step S245, a hysteresis parameter (H2) is determined for the unload period, as also described in greater detail with respect to FIG. 5. It should be appreciated that in step S240 and/or step S245, the bond strength tester may save, transmit, and/or display at least some information and/or data regarding the determined hysteresis parameter H1 and/or H2. Control then advances to step S250.

In step S250, a plasticity parameter (P) is determined from the relaxed bond state. P is the normalized frequency deviation from initial conditions divided by the maximum load per unit bond area, as described in greater detail with respect to FIG. 5. It should be appreciated that in step S250, the bond strength tester may save, transmit, and/or display at least some information and/or data regarding the determined plasticity parameter, P. Control then advances to step S255.

In step S255, the bond strength tester determines the time dependant changes in the ensemble bond phase states, using the determined parameters, N, H1, H2, and P, as described in greater detail with respect to FIG. 5. It should be appreciated that in step S255, the bond strength tester may save, transmit, and/or display at least some information and/or data regarding the determined parameters, N, H1, H2, or P.

Then, in step S260, the bond strength tester determines the strength of the bond. It should be appreciated that in step S260, the bond strength tester may save, transmit, and/or display at least some information and/or data regarding the determined strength of the bond.

Control then advances to step S265 and the method ends.

In various exemplary embodiments, the bond strength tester also alters the temperature of the bond and/or the bond material in a prescribed fashion while taking temperature data with or without load data and ultrasonic frequency data to determine bond parameters as a function of temperature. In this manner the bond strength tester may identify certain bond strength parameters from load, ultrasonic, and thermal data.

It should be appreciated that the analysis of the bond strength parameters is unique for different bond geometries and bond materials. However, once the unique properties are determined with tests to failure (i.e., parameters from similar tests on calibration samples that are or have been proof tested to failure), the determined failure parameters may be used to predict bond strength for a given bond or ensemble system. In this manner, the bond strength tester may provide an assessment of the future capability of a bonded joint without taking that joint to a near-failure load.

It should also be understood that the method outlined above may be used in successive tests, as described in greater detail with respect to FIG. 5, to provide comparison data and or determine the strength of a bond.

FIG. 3 shows the typical data and/or signal information that is used for determining a value of the non-linearity parameter (N), according to this invention. The data and/or signal information is shown in the form of a curve 305. The slope of the curve 305 (the change in the Normalized Frequency divided by the change in the Load) is N.

As shown in FIG. 3, the sample bond is behaving elastically. Even thought the material is in the elastic range of load, the parameter N measures the higher-order elastic constant associated with non-linearity.

FIG. 4 shows a region of an exemplary stress-strain curve where a bond exhibits nonlinear strain. It should be appreciated that the bond strength tester of this invention is useable to document higher-order bond elasticity properties for all regions of the stress-strain curve.

In the linear region 410 of the stress-strain curve of FIG. 4, the introduction of an incremental load-stress, $d\sigma$, produces a corresponding strain, $d\epsilon$. However, in the nonlinear region 420, the strain is increased beyond that expected from a linear response.

The stress/strain properties are linked to the ultrasonic velocity through the elastic constants and the density. Furthermore, it has been shown that higher order elastic constants are linked to engineering states and properties of applied stress, heat treatment, residual stress, and fatigue.

Using applied stress as an example, we explore the stress-strain equation, which, in various exemplary embodiments, may be visualized through Equation 1, as shown below.

$$\sigma = k_2\epsilon + k_3\epsilon^2 + \ldots = k(\epsilon)\epsilon \qquad \text{Equation 1:}$$

Where:
$\sigma$ is the stress;
$k_2$ is the second order "spring" constant;
$k_3$ is the third order constant; and
$\epsilon$ is the strain.

The ultrasonic velocity is related to the elastic constants ($k(\epsilon)$) and the material density ($\rho$) by Equation 2, as shown below.

$$V^2 = k(\epsilon)/\rho \approx (k_2 + k_3\epsilon)/\rho \qquad \text{Equation 2:}$$

Taking a strain derivative of Equation 2 reveals Equation 3, as shown below.

$$dV/d\epsilon = k_3/(2V\rho) \qquad \text{Equation 3:}$$

Thus, the strain derivative of the velocity of sound is a parameter directly linked to the third-order elastic constant, a fundamental property of the material closely linked to nonlinear material behavior. In this manner, velocity derivatives may be used to determine quantitatively the underlying properties of the bond material, nondestructively.

In various exemplary embodiments, when the load-stress is applied as a ramp, the strain will occur in response, but may exhibit some hysteresis. For that reason, the bond strength tester of this invention determines the time dependency of N for applying the load, holding the load and relaxing the load. The response of N upon loading is used to determine certain other bond strength tester parameters, such as, for example, H1, H2, and P.

FIG. 5 shows an exemplary data run with hysteresis and plasticity. As shown in FIG. 5, the stress-load curve 505 is shown as a function of time for a load period (from 0 to T1), a load-hold period (from T1 to T2), and an unload period (from T2 to T3).

As further shown in FIG. 5, a corresponding change in a normalized frequency (dF/F) 515 increases (from 0 to A) during the load period, shows hysteresis during the load-hold period (from A to B), and decreases during the unload period (from B to C). A certain amount of hysteresis is observed after the unload period, when the load has been released (from C to D). Additionally, the sample exhibits a certain degree of plasticity after the load has been released (from D to 0).

Using the determined change in a normalized frequency, the bond strength tester parameters (N, H1, H2, and P) may be determined from this test for a given maximum stress-load. N is the value of the dF/F curve divided by the change in stress-load from zero. H1 is the difference in dF/F between points A and B, divided by the maximum stress-load. Likewise, H2 is the difference in dF/F between points C and D divided by the maximum stress-load. The plasticity parameter, P, is the difference in dF/F between points D and 0.

In various exemplary embodiments, the bond strength tester parameters are determined for several levels of load-stress. Each level increasing in load-stress well below the required ultimate loads required of the structural bond. In various exemplary embodiments, the stability of the parameters with increasing load-stress is a second level test performed by the bond strength tester.

For example, after initially testing a particular bond, load-stress levels may reveal values for N, H1, H2, and P. Then, starting again at zero load-stress, a second test may be performed, wherein a next load-stress level that is 150% of the initial applied load-stress level is applied to the bond.

After the second test is performed, a set of second bond strength tester parameters (N', H1', H2', and P') may be determined and compared to the corresponding initial bond strength tester parameters. The results of this comparison may then be compared with, for example, determined failure parameters from corresponding results achieved from, for example, a witness bond test wherein the witness bond was pulled to failure after or while being measured by the bond strength tester. In various exemplary embodiments, if the determined or compared parameters vary more than a prescribed level, as determined from the witness tests, the bond may be deemed questionable.

Figure 6:
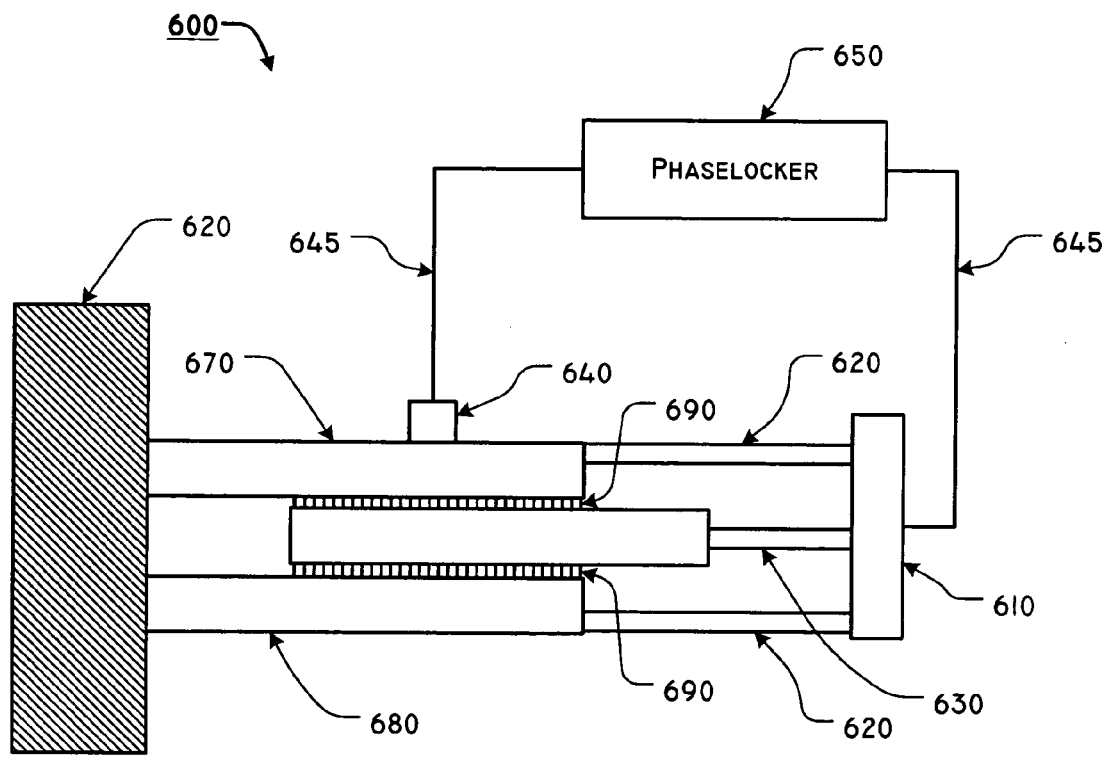
FIG. 6 shows a second exemplary embodiment of a bond strength tester according to this invention.

FIG. 6 shows a second exemplary embodiment of a bond strength tester according to this invention. As shown in FIG. 6, the bond strength tester 600 includes at least some of a coupler 610, a force reactor 620, a stressor 630, a transducer 640, and a phaselocker 650. Additionally, it should be appreciated that the phaselocker 650 may include at least some of an input/output interface 652 (not shown), a data monitoring and acquisition circuit 654 (not shown), a controller 656 (not shown), a memory 658 (not shown), an information database 660 (not shown), a display manager 662 (not shown), and a display 664 (not shown).

It should be understood that each of these elements corresponds to and operates similarly to the bond strength tester 100, the coupler 110, the force reactor 120, the stressor 130, the transducer 140, and the phaselocker 150, the input/output interface 152, the data monitoring and acquisition circuit 154, the controller 156, the memory 158, the information database 160, the display manager 162, and the display 164, as described above with reference to FIG. 1.

However, the bond strength tester 600, as shown in FIG. 6, has been configured to measure shear bond strength between a first bondplate 670 and a second bondplate 680, which are bonded by a bond material 690. Using the bond strength tester 600, measurements are taken the same manner as described above with reference to FIGS. 1 and 2, except that the load or stress is applied parallel to the line of the bond 690.

While this invention has been described in conjunction with the exemplary embodiments outlined above, it will be apparent by those of ordinary skill in the art that various changes, alternatives, modifications, and variations may be made without departing from the spirit and scope of the invention. For example, different acoustic waves such as guided waves or shear waves may be used for this device. The stressing force generated by the stressor 130 may be generated and measured externally by pulling on the coupler 110. The stressor 130 may determine other strength properties. The coupler 110 may apply heat or cooling to determine acoustic changes in the bonded ensemble as a thermal derivative in contrast or in parallel to the stress derivative.

Additionally, it should be understood that the specific location of the various elements included in the bond strength tester is for a basic understanding of the elements included in the bond strength tester and is not to be viewed as limiting the placement of the described elements.

Accordingly, the exemplary embodiments of the invention, as set forth above, are intended to be illustrative, not limiting. Various changes may be made without departing from the spirit and scope of the invention and it is intended that the appended claims be interpreted as including the foregoing as well as other equivalent changes and modifications.

What is claimed is:

1. A non-destructive bond strength tester for determining certain bond strength parameters of a bonded component without destroying the bonded component, comprising:
   an ultrasonic phaselocker for generating a measurement signal used to determine bond properties;
   an ultrasonic transducer for converting the measurement signal into an acoustic wave applied to a material including a bond;
   a loading device that is capable of applying stress-loads to the bond;
   a controller for controlling the loading device;
   a data recorder to acquire measurement data including the measurement signal from the phaselocker, load data from the controller, and a recording time; and
   data processing circuitry to analyze the measurement data and calculate certain bond strength parameters associated with elastic properties of the bond.

2. The non-destructive bond strength tester of claim 1, wherein the phaselocker is a pulsed-phase-locked loop.

3. The non-destructive bond strength tester of claim 1, wherein the phaselocker is a transmission/reflection oscillator ultrasonic spectrometer.

4. The non-destructive bond strength tester of claim 1, wherein the phaselocker is coupled to the bonded component via the ultrasonic transducer.

5. The non-destructive bond strength tester of claim 1, wherein the bond strength tester is capable of altering a temperature of the bond.

6. The non-destructive bond strength tester of claim 1, wherein the loading device comprises:
   a force reactor capable of being attached to at least a portion of the bonded component;
   a stressor capable of applying a force to the bonded component;
   a coupler, wherein the coupler couples the force reactor and the stressor, such that at least the stressor is capable of being actuated and/or manipulated by the controller to apply a force to the bonded component.

7. The non-destructive bond strength tester of claim 1, wherein the transducer is capable of generating a compressional or shear wave as a pulse, a tone burst, a continuous wave, or a guided wave.

8. The non-destructive bond strength tester of claim 1, wherein the transducer includes multiple transducers.

9. The non-destructive bond strength tester of claim 1, wherein the phaselocker includes at least some of:
   an input/output interface;
   a data monitoring and acquisition circuit that is capable of monitoring at least some incoming data and/or signal information from the transducer;
   a memory that is capable of storing at least some ultrasonic wave propagation data and determination software;

an information database that is capable of data and/or signal processing, generation, interpretation, or analysis information;

a controller coupled to the phaselocker, the input/output interface, the data monitoring and acquisition circuit, the memory, the information database, the display manager, and the display, and configured to be capable of managing reading data from and writing data to the memory, driving and managing the transmission of data and/or signal information to and the reception of data and/or signal information from the transducer, and driving and managing operation of the force reactor and the stressor.

10. The non-destructive bond strength tester of claim 1, wherein the phaselocker is one of a high-resolution ultrasonic interferometer system, a transmission/reflection oscillator ultrasonic spectrometer, a phase-locked-loop, or a pulsed-phase-locked-loop ultrasonic spectrometer.

11. The non-destructive bond strength tester of claim 1, wherein the data processing circuitry is configured to extract non-linear velocity derivatives from changes in the measurement signal as a function of load or strain.

12. The non-destructive bond strength tester of claim 1, wherein the bond strength tester is capable of altering the temperature of the bond in a prescribed fashion while taking at least some temperature data, load data, ultrasonic data, and ultrasonic frequency data to determine bond parameters as a function of temperature.

13. The non-destructive bond strength tester of claim 1, wherein the data processing circuitry is configured to predict a strength of the bond based on the calculate bond strength parameters.

14. The non-destructive bond strength tester of claim 1, wherein the data processing circuitry is configured to analyze the measurement signal to determine creep under load and recovery of plasticity after load reduction.

15. The non-destructive bond strength tester of claim 1, wherein the bond strength parameters reflect linear and non-linear elastic properties of the bond.

16. The non-destructive bond strength tester of claim 1, wherein the bond strength parameters include a non-linearity parameter, a hysteresis parameter, and a plasticity parameter.

17. The non-destructive bond strength tester of claim 1, wherein the data processing circuitry is configured to compare the calculated bond strength parameters with predetermined bond strength parameters to predict a potential bond strength deficiency.

18. A method for non-destructive testing the strength of a bond of a bonded component, comprising:

coupling a phaselocker, via a transducer, to a bonded component to create an ensemble system;

acquiring at least some load data and ultrasonic frequency data for the ensemble system during an initial state;

applying a load to the bonded component during a load period by placing the bond under tension or compression, thereby applying stress to the bond;

acquiring at least some load data and ultrasonic frequency data from the ensemble system during the load period;

maintaining the load on the bonded component during a load-hold period;

acquiring at least some load data and ultrasonic frequency data from the ensemble system during the load-hold period;

removing the load on the bonded component during an unload period;

acquiring at least some load data and ultrasonic frequency data from system during the unload period;

acquiring at least some load data and ultrasonic frequency data for the ensemble system after the load on the bonded component has been removed during a relaxation period;

determining a non-linearity parameter from at least some of the acquired data; and assessing the strength of the bond based on the determined non-linearity parameter.

19. The method of claim 18, wherein acquiring includes acquiring via a data monitoring and acquisition circuit.

20. The method of claim 18, further including saving at least some of the information and/or data regarding the acquired load data and ultrasonic frequency data and/or at least some of the information and/or data regarding one or more determined parameters to a memory.

21. The method of claim 18, further including transmitting at least some of the information and/or data regarding the acquired load data and ultrasonic frequency data and/or at least some of the information and/or data regarding one or more determined parameters.

22. The method of claim 18, further including displaying at least some of the information and/or data regarding the acquired load data and ultrasonic frequency data and/or at least some of the information and/or data regarding one or more determined parameters on a display.

23. The method of claim 18, further including:
altering a temperature of the bond in a prescribed fashion;
acquiring at least some temperature data for the ensemble system; and
assessing the strength of the bond based on one or more determined parameters and the temperature data.

24. The method of claim 18, further including:
comparing one or more determined parameters to one or more determined parameters from a prior test of a bond; and
assessing the strength of the bond based on the comparison.

25. The method of claim 18, further comprising:
determining a first hysteresis parameter for the load-hold period from at least some of the acquired data;
determining a second hysteresis parameter for the unload period from at least some of the acquired data; and
determining a plasticity parameter for the relaxation period from at least some of the acquired data,
wherein the assessment of the bond strength is based on one or more of the determined parameters and one or more failure parameters associated with the bond.

26. The method of claim 18, further comprising:
extracting non-linear velocity derivatives from changes in at least some of the acquired data as a function of load or strain.

27. The method of claim 18, further comprising:
predicting the strength of the bond based on the determined non-linearity parameter.

28. The method in claim 18, wherein the non-linearity parameter is an indicator of linear and non-linear elastic properties of the bond.

29. A method for non-destructively determining at least some bond strength parameters for a bond of a bonded component, comprising:

coupling a phaselocker, via a transducer, to a bonded component to create an ensemble system;

acquiring at least some load data and ultrasonic frequency data for the ensemble system during an initial state;

applying a load to the bonded component during a load period by placing the bond under tension or compression, thereby applying stress to the bond;

acquiring at least some load data and ultrasonic frequency data from the ensemble system during the load period;
maintaining the load on the bonded component during a load-hold period;
acquiring a least some load data and ultrasonic frequency data from the ensemble system during the load-hold period;
removing the load on the bonded component during an unload period;
acquiring at least some load data and ultrasonic frequency data from the ensemble system during the unload period;
acquiring at least some load data and ultrasonic frequency data for the ensemble system after the load on the bonded component has been removed during a relaxation period; and
determining a linearity parameter from at least some of the acquired data.

30. The method of claim 29, further comprising:
determining a first hysteresis parameter for the load-hold period from at least some of the acquired data;
determining a second hysteresis parameter for the unload period from at least some of the acquired data; and
determining a plasticity parameter for the relaxation period from at least some of the acquired data.

31. The method of claim 29, wherein the linearity parameter is associated with linear and non-linear properties of the bond.

32. The method of claim 29, further comprising:
extracting non-linear velocity derivatives from changes in at least some of the acquired data as a function of load or strain.

* * * * *